United States Patent

Chasan et al.

Patent Number: 5,613,853
Date of Patent: Mar. 25, 1997

[54] MANDIBULAR FIXATION SYSTEM

[75] Inventors: Paul E. Chasan, Salt Lake City, Utah; Mark S. Chasan, Redondo Beach, Calif.

[73] Assignee: Mango Enterprises, Inc., Marina Del Rey, Calif.

[21] Appl. No.: 188,676

[22] Filed: Jan. 31, 1994

Related U.S. Application Data

[63] Continuation of Ser. No. 951,779, Sep. 28, 1992, abandoned.
[51] Int. Cl.⁶ ........................................ A61C 5/00
[52] U.S. Cl. ........................................ 433/215
[58] Field of Search .................. 433/18, 22, 24, 433/215; 24/16 PB

[56] References Cited

U.S. PATENT DOCUMENTS

| | | | |
|---|---|---|---|
| 3,337,957 | 8/1967 | Reed | 433/215 |
| 3,486,201 | 12/1969 | Bourne | 24/16 PB |
| 3,739,430 | 6/1973 | Kohke | 24/16 PB |
| 3,855,670 | 12/1974 | Brudy | 24/16 PB |
| 3,913,228 | 10/1975 | Wallsheim | 433/18 |
| 4,202,328 | 5/1980 | Sukkarie | 433/18 X |
| 4,318,694 | 3/1982 | Klein | 433/18 X |
| 4,413,380 | 11/1983 | Suzuki | 24/16 PB |

*Primary Examiner*—Nicholas D. Lucchesi
*Attorney, Agent, or Firm*—Irving Keschner

[57] ABSTRACT

A method for fixing a patient's mandible such that a fracture therein can be healed. A plastic cable tie is utilized to attach an arch bar to the patient's upper and lower teeth. The shape of the cable tie is designed to easily fit between the teeth and to have a low profile to allow for maximum patient comfort.

4 Claims, 2 Drawing Sheets

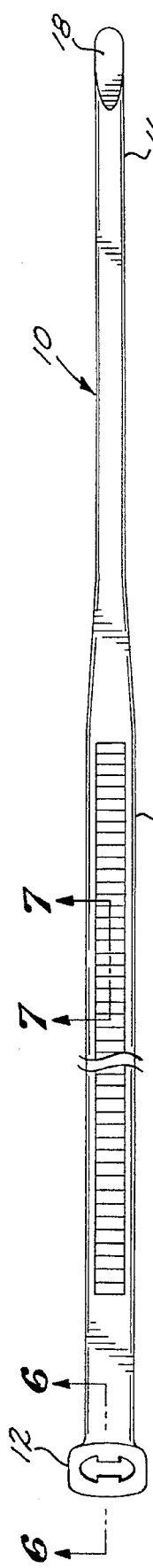
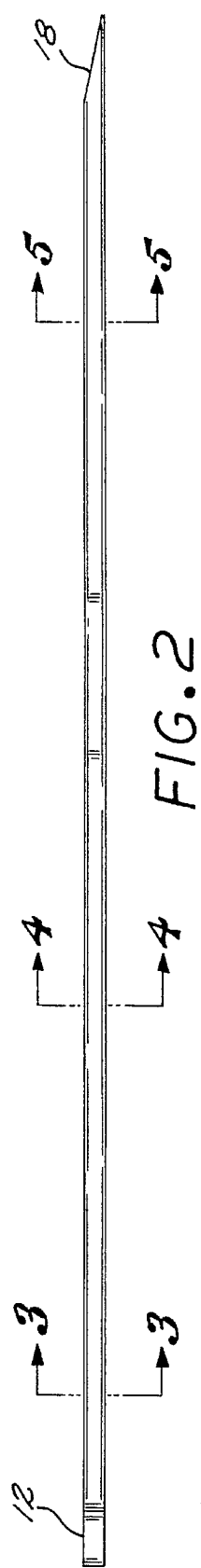
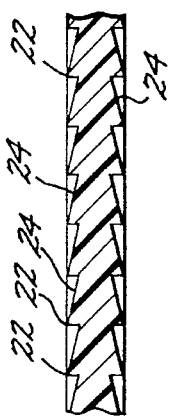

MANDIBULAR FIXATION SYSTEM

CROSS-REFERENCE TO RELATED APPLICATION

This application is a continuation of application Ser. No. 07/951,779, filed Sep. 28, 1992, now abandoned.

BACKGROUND OF THE INVENTION

1. Field of the Invention

The present invention relates to a mandibular fixation system and, in particular, a plastic cable tie for securing an arch bar to the patient's teeth.

2. Description of the Prior Art

The current treatment for most mandibular fractures as well as some facial fractures and orthognathic abnormalities involves the application of arch bars to the upper and lower teeth by using surgical wire. Once applied the upper and lower arch bars are fixed together by the use of rubber bands. This effectively immobilizes the mandible allowing healing of the fracture much like a cast. In cases of facial fractures and orthognathic abnormalities, the immobile mandible serves as a scaffold for the reduction of facial fractures or the repositioning of maxillary deformities.

A major disadvantage in the application of the arch bars is the use of surgical wire. Surgical wire causes many problems for the patient as well as the physician. First, surgical wire is stiff and has sharp ends which often results in accidental finger sticks to the physician who is applying the arch bar. In addition, the population of patients who are admitted to hospital emergency rooms with fractured jaws have a much higher incidence of blood-borne communicable diseases, names AIDS and hepatitis. Second, surgical wire is difficult to use, and, therefore, it takes a considerable amount of time to secure the arch bar, typically 45 to 60 minutes. Third, surgical wire is brittle and commonly breaks, thus repeat applications of wire are not uncommon. Lastly, once applied, the wire often pokes the patient's cheek and gum making the arch bar very uncomfortable. Currently, bone wax is used to cover the sharp ends, but it tends to come off the ends quickly giving the patient only transient relief.

What is thus desired is to provide a technique of securing arch bars to a patient's upper and lower teeth which avoids the disadvantages noted above.

SUMMARY OF THE PRESENT INVENTION

The present invention provides a method for fixing a patient's mandible such that a fracture therein can be healed. A novel plastic cable tie is utilized to attach an arch bar to the patient's upper and lower teeth, whether the front (incisors), canines, molars or premolars, the shape of the cable tie being designed to easily fit between the teeth and to have a low profile for maximum patient comfort. In addition, the cable tie is easier to use and requires less time in its application, is less brittle and will decrease the incidence of breakage since it is made of a plastic polymer. The size of the cable tie is smaller than the commercially available cable ties, typically being ¼ the width of the smallest available cable tie. The shape of the cable tie is specifically designed to fit between teeth while maintaining maximal strength; its cross-section being essentially elliptical in order to accommodate the naturally occurring elliptical space between teeth. The leader of the cable tie is stiff, the end being cut at an angle so it is semi-sharp i.e. sharp enough to pass through loose gingival tissue when force is applied directly to it, but not sharp enough to cut someone's finger when handling or manipulating it or to poke the gums and check of the patient. In addition, the cable tie locking mechanism has two barbs for extra locking strength while the serration have a low profile and channeled so the cable part passes through the tissue with minimal friction. The head of the cable tie also has a low profile to enable the cable tie to lay flatter, thus allowing maximal comfort for the patient.

This new cable tie described hereinabove substantially eliminates the risk of accidental finger pricks during the application of arch bars, markedly decreases the time needed to apply the arch bar, and is more comfortable to the patient. The cable tie of the present invention is simple and economical to manufacture.

BRIEF DESCRIPTION OF THE DRAWING

For better understanding of the present invention as well as other objects and further features thereof, reference is made to the following description which is to be read in conjunction with the accompanying drawing wherein;

FIG. 1 is a plan view of the novel cable tie of the present invention;

FIG. 2 is a side elevational view of the tie shown in FIG.

FIG. 3 is a sectional view along line 3—3 of FIG. 2;

FIG. 4 is a sectional view along line 4—4 of FIG. 2;

FIG. 5 is a sectional view along line 5—5 of FIG. 2;

FIG. 6 is a sectional view along line 6—6 of FIG. 1;

FIG. 7 is a sectional view along line 7—7 of FIG. 1;

DETAILED DESCRIPTION OF THE INVENTION

Figure 8:
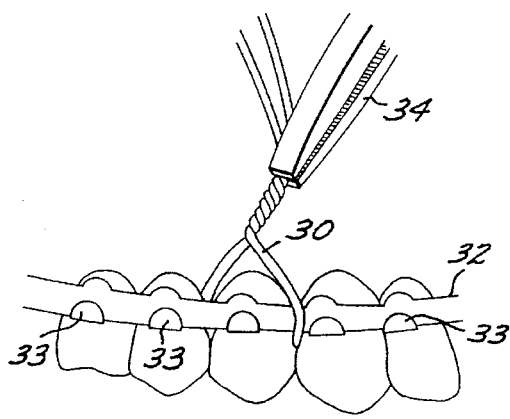
FIG. 8 is a perspective view illustrating the attachment of an arch bar to the front upper teeth of a patient using surgical wire.

Referring now to FIGS. 1–4, cable tie 10, of the present invention comprises three separate portions: head portion 12, a portion 14 having serrations thereon and a leader portion 16.

The width of cable tie 10 is much narrower then ties currently available, typically one-forth the size. Cable tie 10 is specifically shaped to fit between a patient's teeth while retaining maximum strength, thus the cross-section is essentially elliptical, as shown in FIG. 3–5, in order to accommodate the naturally occurring elliptical space between the teeth. The leader is stiff, the end 18 being cut at an angle so it is semi-sharp i.e. sharp enough to pass through loose gingival tissue when force is directly applied to it, but not sharp enough to cut a user's finger when handling or manipulating it. As shown in FIG. 6, the locking head 12 has two barbs 19 and 20 to provide extra locking strength, conventional ties typically having only one locking barb. The serrations 22 are smaller sized (low profile) and have adjacent channels 24 such that the cable tie portion 14 passes through gum tissue with minimal interference.

Head portion 12 has also been reduced in size to present a low profile, making the cable tie lie flatter and thus increasing the comfort level for a patient. In particular, the thickness of head 12 as shown in FIG. 2 is substantially the same thickness as portion 14 adjacent thereto.

FIG. 8 illustrates the current procedures for most mandibular fractures as well as some facial fractures and orthognathic abnormalities. In particular, surgical wire 30 is wound about arch bar 32 by gripping tool 34 in a manner such that the arch bar 32 is secured to the upper front teeth in the example illustrated. Arch bar 32 has a plurality of vertical hook members extending from the surface thereof.

Figure 9:
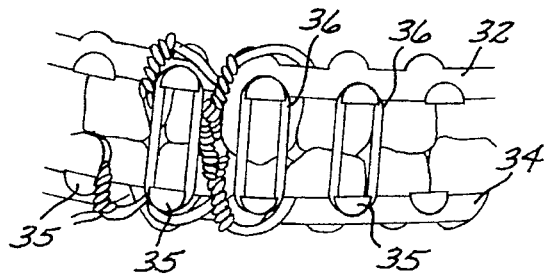
FIG. 9 is a perspective view illustrating the immobilization of the patients jaw using surgical wire.

FIG. 9 illustrates the situation wherein both arch bar 32 and an arch bar 34, arch bar 34 being secured to the lower set of front teeth in the example illustrated and having a plurality of downwardly extending hook members 35 formed thereon, are fixed together by elastic members, such as rubber bands, 36 looping about corresponding hook members 33 and 35 as illustrated.

Figure 10:
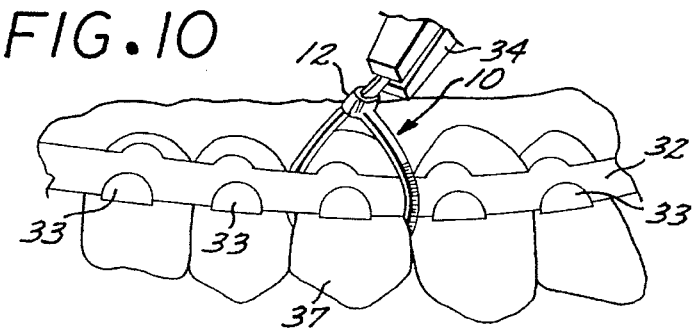
FIG. 10 is a perspective view illustrating the attachment of an arch bar to the front upper teeth of a patient using the novel cable tie of the present invention.
Figure 11:
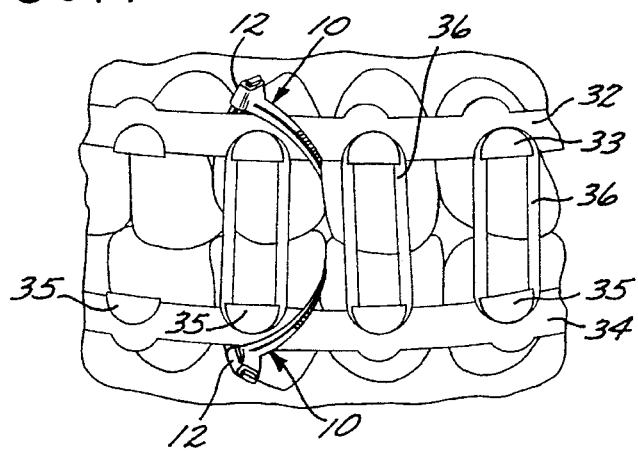
FIG. 11 is perspective view illustrating the immobilization of a patient's jaw using the novel cable tie of the present invention.

FIG. 10 illustrates the use of tool 34 to install cable 10 of the present invention to secure arch bar 32 to the upper front teeth in the example illustrated, the cable tie passing through adjacent edges of tooth 37, and FIG. 11 illustrates arch bars 32 and 34 secured to the patients upper front teeth and lower front teeth, respectively , the arch bars being fixed together by elastic members 36. The excess portion of leader portion 16 of both cable ties 10 are removed by the tool. FIG. 11 illustrates the completion of the mandibular fixation system, both cable ties 10 extending along the corresponding arch bars and teeth.

Although one cable tie is illustrated to secure each arch bar 32 and 34, additional cable ties can be utilized.

The present invention thus provides an improved mandibular fixation system which utilizes a plastic cable tie to secure arch bars to a patient's teeth, the cable tie being designed to easily fit between the teeth of the patient and provide maximum patient comfort while also providing a degree of safety to the dentist or other health provider installing the mandibular fixation system.

While the invention has been described with reference to its preferred embodiments, it will understood by those skilled in the art that various changes may be made and equivalents may be substituted for elements thereof without departing from the true spirit and scope of the invention. In addition, many modifications may be made to adapt a particular situation or material to the teachings of the invention without departing from its essential teachings.

What is claimed is:

1. A method for fixing the mandible of a patient to allow fractures therein to heal comprising the steps of:

positioning an arch bar on a first set of the patient's teeth;

inserting a cable tie in the space between first and second adjacent teeth and between said second tooth and a third tooth adjacent said second tooth in a manner such that the cable tie overlies a portion of said arch bar;

locking the cable tie in a manner to secure the arch bar to said second tooth;

providing a plurality of additional cable ties to secure said arch bar to other of said patient's teeth in said first set of teeth;

positioning an arch bar on a second set of patient's teeth adjacent said first set of teeth and secured thereto by a cable tie, each arch bar having a plurality of hook members formed therein; and engaging adjacent hook members on each arch bar with a resilient member whereby the patient's mandible is fixed.

2. A method for fixing the mandible of a patient to allow fractures therein to heal comprising the steps of:

positioning an arch bar on a first set of the patient's teeth;

inserting a cable tie in the space between first and second adjacent teeth and between said second tooth and a third tooth adjacent said second tooth in a manner such that the cable tie overlies a portion of said arch bar, a portion of said cable tie having an elliptical cross-section; and locking the cable tie in a manner to secure the arch bar to said second tooth.

3. A method for fixing the mandible of a patient to allow fractures therein to heal comprising the steps of:

positioning an arch bar on a first set of the patient's teeth;

inserting a cable tie in the space between first and second adjacent teeth and between said second tooth and a third tooth adjacent said second tooth in a manner such that the cable tie overlies a portion of said arch bar, said cable tie comprising a head portion and a leader portion, a portion of said cable tie having an elliptical cross-section, said head portion having a low profile; and locking the cable tie in a manner to secure the arch bar to said second tooth.

4. The method of claim 3 wherein said leader portion is substantially rigid, the end being cut at an angle to allow the tie to pass through gingival tissue when force is applied directly to it.

* * * * *